(12) United States Patent
Zen

(10) Patent No.: US 6,296,864 B1
(45) Date of Patent: Oct. 2, 2001

(54) PESTICIDAL COMPOSITION

(75) Inventor: Shigekazu Zen, Minoo (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 08/961,499

(22) Filed: Oct. 30, 1997

(30) Foreign Application Priority Data

Nov. 1, 1996 (JP) .................................................. 8-291979

(51) Int. Cl.$^7$ ........................................................ A01N 25/02
(52) U.S. Cl. ........................ 424/405; 514/113; 514/345; 514/531
(58) Field of Search ............................... 504/116; 424/405; 514/75, 345, 531, 478, 532, 112–115, 941, 943

(56) References Cited

U.S. PATENT DOCUMENTS

| | | | | |
|---|---|---|---|---|
| 464,092 | * | 12/1891 | Burton | 504/357 |
| 663,071 | * | 12/1900 | Bejan | 504/357 |
| 2,552,187 | * | 5/1951 | Koomin | 504/356 |
| 2,768,111 | | 10/1956 | Butler et al. | 167/43 |
| 3,990,884 | * | 11/1976 | Barker | 71/111 |
| 4,617,318 | | 10/1986 | Abdel | 574/520 |
| 4,774,369 | * | 9/1988 | Matsuo et al. | 568/873 |
| 5,084,087 | | 1/1992 | Hazen et al. | 71/123 |
| 5,190,745 | | 3/1993 | Dohara et al. | 424/45 |

FOREIGN PATENT DOCUMENTS

| | | | |
|---|---|---|---|
| 8652982 | | 2/1984 | (AU) . |
| 2072104 | * | 4/1991 | (CA) . |
| 2051815 | | 5/1971 | (DE) . |
| 3343092 | | 6/1985 | (DE) . |
| 3609919 | | 10/1987 | (DE) . |
| 0394847 | | 10/1990 | (EP) . |
| 2373231 | | 7/1978 | (FR) . |
| 2058569 | | 12/1993 | (GB) . |
| 2267826 | | 12/1993 | (GB) . |
| 62240601 | * | 10/1987 | (JP) . |
| 9106215 | | 5/1991 | (WO) . |
| 9601047 | | 1/1996 | (WO) . |

OTHER PUBLICATIONS

GB 995 383 A (Rohm & Haas) Claims 1–9.

* cited by examiner

Primary Examiner—Neil S. Levy
(74) Attorney, Agent, or Firm—Sughrue, Mion, Zinn, Macpeak & Seas, PLLC

(57) ABSTRACT

A pesticidal composition comprising (a) 1 to 50% by weight of a lipophilic compound as a pesticidally active ingredient, (b) 0.1 to 10% by weight of at least one nonionic surfactant, (c) 0.3 to 4% by weight of at least one anionic surfactant selected from the group consisting of alkylarylsulfonic acid salts and alkylbiphenylsulfonic acid salts, (d) 15 to 40% by weight of a fatty acid ester represented by the formula:

RCOOR'  [1]

wherein R is an alkyl group having 2 to 21 carbon atoms or an alkenyl group having 2 to 21 carbon atoms, and R' is an alkyl group having 1 to 6 carbon atoms, and (e) 20 to 80% by weight of an aromatic hydrocarbon solvent, which shows a good emulsion stability when diluted with water, has a good low-temperature storage stability, and is only slightly irritant.

32 Claims, No Drawings

PESTICIDAL COMPOSITION

The present invention relates to a pesticidal composition, in particular, a slightly irritant pesticidal emulsifiable concentrate which shows good emulsion stability when diluted with water.

A compound as a pesticidally active ingredient is usually used after being formulated into any of various conveniently usable forms. One of conventional formulations of a lipophilic compound used as a pesticidally active ingredient is an emulsifiable concentrate.

A pesticidal emulsifiable concentrate is usually composed of a lipophilic compound as a pesticidally active ingredient, a surfactant and an organic solvent and is used after being diluted with water. In order to enhance the emulsion stability of an emulsion obtained by dilution with water and reduce toxicity to human beings and animals and phytotoxicity to crops, depending on the kind of the compound as a pesticidally active ingredient, choice of the surfactant, choice of the organic solvent and their combination can be made variously.

The present invention was attained in order to provide a pesticidal composition which shows a good emulsion stability when diluted with water and is only slightly irritant.

The present invention provides a pesticidal composition comprising (a) 1 to 50% by weight of a lipophilic compound as a pesticidally active ingredient, (b) 0.1 to 10% by weight of at least one nonionic surfactant, (c) 0.3 to 4% by weight of at least one anionic surfactant selected from the group consisting of alkylarylsulfonic acid salts and alkylbiphenylsulfonic acid salts, (d) 15 to 40% by weight of a fatty acid ester represented by the formula:

RCOOR'  [1]

wherein R is an alkyl group having 2 to 21 carbon atoms or an alkenyl group having 2 to 21 carbon atoms, and R' is an alkyl group having 1 to 6 carbon atoms, and (e) 20 to 80% by weight of an aromatic hydrocarbon solvent.

The pesticidal composition of the present invention shows a good emulsion stability when diluted with water. Furthermore, the pesticidal composition of the present invention is good also in low-temperature storage stability and is only slightly irritant.

The compound used in the present invention as a pesticidally active ingredient is not particularly limited so long as it is lipophilic and soluble in aromatic hydrocarbon solvents. The compound includes, for example, insecticides and insect growth regulators. Preferable examples thereof are Pyriproxyfen [4-phenoxy-phenyl 2-(2-pyridyloxy)propyl ether] and compounds represented by the formula:

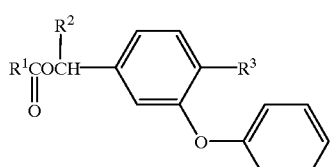

[2]

wherein $R^1$ is a group represented by the formula:

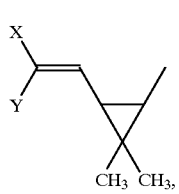

[3]

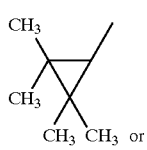

[4]

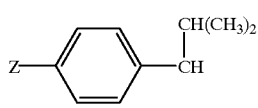

[5]

[wherein X and Y, which may be the same or different, are methyl groups, trifluoromethyl groups, halogen atoms (e.g. fluorine, chlorine, bromine, iodine) or alkoxycarbonyl groups whose alkoxy group has 1 to 4 carbon atoms, and Z is a halogen atom (e.g. fluorine, chlorine, bromine, iodine) or a difluoromethoxy group], $R^2$ is a hydrogen atom or a cyano group, and $R^3$ is a hydrogen atom or a fluorine atom.

Specific examples of the compounds [2] are pyrethroid compounds such as Fenvalerate [α-cyano-3-phenoxybenzyl 2-(4-chlorophenyl)-3-methylbutyrate], Esfenvalerate [(S)-α-cyano-3-phenoxybenzyl (S)-2-(4-chlorophenyl)-3-methylbutyrate], Fenpropathrine [α-cyano-3-phenoxybenzyl 2,2,3,3-tetramethylcyclopropanecarboxylate], Permethrin [3-phenoxybenzyl 3-(2,2-dichlorovinyl)-2,2-dimethylcyclopropanecarboxylate], Cypermethrin [α-cyano-3-phenoxybenzyl 3-(2,2-dichlorovinyl)-2,2-dimethylcyclopropanecarboxylate], d-Phenothrin [3-phenoxybenzyl (1R)-chrysanthemate], Cyphenothrin [α-cyano-3-phenoxybenzyl (1R)-chrysanthemate], Cyhalothrin [α-cyano-3-phenoxybenzyl (Z)-(2-chloro-3,3,3-trifluoropropenyl)-2,2-dimethylcyclopropanecarboxylate], Cyfluthrin [α-cyano-4-fluoro-3-phenoxybenzyl 3-(2,2-dichlorovinyl)-2,2-dimethylcyclopropanecarboxylate], Flucythrinate [α-cyano-3-phenoxybenzyl (S)-2-(4-difluoromethoxyphenyl)-3-methylbutyrate], etc.

In addition to these compounds, pyrethroid compounds such as Tralomethrin [(S)-α-cyano- 3-phenoxy-benzyl 2,2-dimethyl-3-(1,2,2,2-tetrabromoethyl)cyclopropanecarboxylate], Allethrin [3-allyl-2-methyl-4-oxo-2-cyclopentenyl crysanthemate], Cycloprothrin [α-cyano-3-phenoxybenzyl 2,2-dichloro-1-(4-ethoxyphenyl) cyclopropanecarboxylate], Fluvalinate [α-cyano-3-phenoxybenzyl N-(2-chloro-α,α,α-trifluoro-p-tolyl) valinate], Ethofenprox [2-(4-ethoxyphenyl)-2-methylpropyl 3-phenoxybenzyl ether], etc.; organophosphorus compounds such as Fenitrothion, Cyanophos, Fenthion, Diazinon, etc.; and carbamate compounds such as Fenobucarb, Alanycarb, Carbosulfan, etc. are also preferable as the compound used as a pesticidally active ingredient in the pesticidal composition of the present invention.

The compound as a pesticidally active ingredient is contained in the pesticidal composition of the present invention in an amount of usually 1 to 50% by weight, preferably 1 to 30% by weight.

The surfactants used in the present invention are both the nonionic surfactant(s) and the anionic surfactant(s). As the nonionic surfactant(s), there are preferably used one or more nonionic surfactants selected from the group consisting of polyoxyethylene polyoxypropylene block polymers, polyoxyethylene polyoxypropylene alkyl aryl ethers, polyoxyethylene polyoxypropylene alkyl ethers, polyoxyethylene polyoxypropylene polyaryl ethers, and fatty acid esters of polyoxyethylene polyoxypropylene block polymers. As the anionic surfactant(s), there are used one or more anionic surfactants selected from the group consisting of alkylarylsulfonic acid salts and alkylbiphenylsulfonic acid salts.

Of the above-exemplified nonionic surfactants, those having a molecular weight of approximately 500–3,000 are preferable. More preferable are polyoxyethylene polyoxypropylene block polymers having a HLB of 10 to 14, polyoxyethylene polyoxypropylene alkyl aryl ethers (e.g. polyoxyethylene polyoxypropylene nonyl phenol ethers) having a HLB of 9 to 14, polyoxyethylene polyoxypropylene alkyl ethers (e.g. polyoxyethylene polyoxypropylene octyl ethers) having a HLB of 9 to 12, polyoxyethylene polyoxypropylene polyaryl ethers (e.g. tristyrylphenyl ethers of polyoxyethylene polyoxypropylenes, and distyrylphenyl ethers of polyoxyethylene polyoxypropylenes) having a HLB of 9 to 14, and fatty acid esters of polyoxyethylene polyoxypropylene block polymers (e.g. stearic acid esters of polyoxyethylene polyoxypropylene block polymers) having a HLB of 9 to 13.

It is also preferable to use other nonionic surfactants in combination with the above-exemplified nonionic surfactants. The other nonionic surfactants include polyoxyethylene alkylphenyl ethers, polyoxyethylene vegetable oils, polyoxyethylene hardened vegetable oils, polyoxyethylene tristyrylphenyl ethers, polyoxyethylene alkyl aryl ether polymers, polyoxyethylene fatty acid esters, polyoxyethylene alkyl ethers, polyoxyethylene distyrylphenyl ether polymers, polyoxyethylene tristyrylphenylphosphate diesters, polyoxyalkylphenol ethers, fatty acid alcohol polyglycol ethers, glycerol fatty acid esters, etc.

The nonionic surfactant(s) is contained in the pesticidal composition of the present invention in an amount of usually 0.1 to 10% by weight, preferably 0.4 to 7% by weight.

The anionic surfactant(s) used in the present invention is at least one alkylarylsulfonic acid salt and/or at least one alkylbiphenylsulfonic acid salt. Although the alkyl group of the alkylarylsulfonic acid salt is not particularly limited so long as the alkylarylsulfonic acid salt has surface activity, it is usually an alkyl group having approximately 8–15 carbon atoms. The salt thereof is also not particularly limited so long as the alkylarylsulfonic acid salt has surface activity. Examples of the salt are alkaline earth metal salts such as calcium salt, magnesium salt, etc., and amine salts. The alkylarylsulfonic acid salts include alkylbenzenesulfonic acid salts, a specific example of which is calcium dodecylbenzenesulfonate.

Although the alkyl group of the alkylbiphenylsulfonic acid salt is not particularly limited so long as the alkylbiphenylsulfonic acid salt has surface activity, it is usually an alkyl group having approximately 7–15 carbon atoms. The salt thereof is also not particularly limited so long as the alkylbiphenylsulfonic acid salt has surface activity. Examples of the salt are alkaline earth metal salts such as calcium salt, magnesium salt, etc., and amine salts. A specific example of the alkylbiphenylsulfonic acid salt is dodecyldiphenyl oxide disulfonate calcium salt.

The anionic surfactant(s) is contained in the pesticidal composition of the present invention in an amount of usually 0.3 to 4% by weight, preferably 0.5 to 3.5% by weight.

In addition, the pesticidal composition of the present invention may contain anionic surfactants other than the above-exemplified anionic surfactants. The other anionic surfactants include calcium polyoxyethylene alkylphenylsulfonates, calcium polyoxyethylene alkylphenylphosphates, calcium polyoxyethylene tristyrylphenylphosphates, calcium dialkylsulfosuccinates, ammonium dialkylsulfosuccinates, etc.

The organic solvents used in the present invention are both the fatty acid ester of the formula:

$$RCOOR' \qquad [1]$$

[wherein R is an alkyl group having 2 to 21 carbon atoms or an alkenyl group having 2 to 21 carbon atoms, and R' is an alkyl group having 1 to 6 carbon atoms; here, the term "alkenyl group" for R is used not for expressing an alkenyl group in a narrow sence which has only one double bond, but for expressing an alkenyl group including so-called alkadienyl groups, alkatrienyl groups and the like, which have two or more double bonds], and the aromatic hydrocarbon. The fatty acid ester includes methyl esters, ethyl esters, isopropyl esters, butyl esters, isobutyl esters, isoamyl esters and the like of carboxylic acids [e.g. propionic acid, butyric acid, isovaleric acid, lauric acid, myristic acid, palmitic acid, capric acid, oleic acid, linoleic acid and linolenic acid], for example, butyl propionate, isoamyl propionate, ethyl butyrate, butyl butyrate, isoamyl butyrate, isoamyl isovalerate, methyl laurate, isopropyl myristate, isopropyl palmitate, methyl caprate, methyl oleate, isobutyl oleate, methyl linoleate, methyl linolenate, and mixtures thereof. The aromatic hydrocarbon includes alkylbenzenes (e.g. xylene and tetramethylbenzene), alkylnaphthalenes (e.g. methylnaphthalene), naphthalene, diphenylethane, phenylxylylethane, and mixtures thereof. As the aromatic hydrocarbon, those having 8 to 20 carbon atoms are usually used.

The fatty acid ester is contained in the pesticidal composition of the present invention in an amount of usually 15 to 40% by weight, preferably 20 to 40% by weight.

The aromatic hydrocarbon is contained in the composition of the present invention in an amount of usually 20 to 80% by weight, preferably 35 to 70% by weight.

The ratio of the fatty acid ester to the aromatic hydrocarbon ranges preferably from 1:5 to 1:1 by weight, more preferably from 1:4 to 4:5 by weight.

If necessary, the composition of the present invention may contain other additives, for example, antioxidants such as 3-/2-t-butyl-4-hydroxyanisole, butylated hydroxytoluene, etc.; alcohol solvents such as 2-ethylhexanol, etc.; and ketone solvents.

The composition of the present invention is usually used as a formulation for foliage treatment or seed treatment.

For foliage treatment, in general, stems and leaves are sprayed with a dilution prepared by diluting the composition of the present invention approximately 100- to 5,000-fold with water, though the degree of dilution is varied depending on the kind and content of the active ingredient in the present composition. It is also possible to carry out the aerial application of a dilution prepared by diluting the composition of the present invention approximately 10- to 1000-fold with water, by a helicopter.

For seed treatment, seeds are immersed in a dilution prepared by diluting the composition of the present invention approximately 10- to 100-fold with water, or seeds are sprayed with a dilution prepared by diluting the composition of the present invention approximately 2- to 100-fold.

EXAMPLES

The present invention is more concretely illustrated below with reference to examples.

In the following examples, parts are all by weight.

Formulation Example 1

Present inventive composition (1) was obtained by thoroughly mixing the following ingredients in a total amount of 100 parts: 11 parts of Pyriproxyfen, 1.0 part of Soprophor 796/P (a polyoxyethylene polyoxypropylene polyaryl ether having a HLB of 13.5, manufactured by Rhone Poulenc), 5.6 parts of Geronol FF-4-E (a surfactant containing 50 wt % calcium dodecylbenzenesulfonate, manufactured by Rhone Poulenc), 22 parts of methyl oleate and the balance of Solvesso 150 (an aromatic hydrocarbon solvent having 9 to 11 carbon atoms, manufactured by Exxon Chemical Co., Ltd.).

Formulation Example 2

Present inventive composition (2) was obtained by thoroughly mixing the following ingredients in a total amount of 100 parts: 11 parts of Pyriproxyfen, 0.7 part of Soprophor 796/P, 5.9 parts of Geronol FF-4-E, 33 parts of methyl oleate and the balance of Solvesso 150.

Formulation Example 3

Present inventive composition (3) was obtained by thoroughly mixing the following ingredients in a total amount of 100 parts: 11 parts of Pyriproxyfen, 0.55 part of Soprophor 796/P, 4.95 parts of Geronol FF-4-E, 33 parts of methyl oleate and the balance of Solvesso 150.

Formulation Example 4

Present inventive composition (4) was obtained by thoroughly mixing the following ingredients in a total amount of 100 parts: 1 part of Pyriproxyfen, 0.7 part of Soprophor 796/P, 5.9 parts of Geronol FF-4-E, 33 parts of methyl oleate and the balance of Solvesso 150.

Formulation Example 5

Present inventive composition (5) was obtained in exactly the same manner as in Formulation Example 2 except for using 5.5 parts of Fenpropathrine in place of 11 parts of Pyriproxyfen.

Formulation Example 6

Present inventive composition (6) was obtained by thoroughly mixing the following ingredients in a total amount of 100 parts: 5 parts of Fenvalerate, 1.0 part of Soprophor 796/P, 5.6 parts of Geronol FF-4-E, 25 parts of methyl oleate and the balance of Solvesso 150.

Formulation Example 7

Present inventive composition (7) was obtained by thoroughly mixing the following ingredients in a total amount of 100 parts: 3 parts of Fenvalerate, 0.7 part of Soprophor 796/P, 5.9 parts of Geronol FF-4-E, 40 parts of methyl laurate and the balance of Solvesso 150.

Formulation Example 8

Present inventive composition (8) was obtained in exactly the same manner as in Formulation Example 6 except for using 5 parts of Permethrin in place of 5 parts of Fenvalerate.

Formulation Example 9

Present inventive composition (9) was obtained in exactly the same manner as in Formulation Example 1 except for using 11 parts of Fenvalerate in place of 11 parts of Pyriproxyfen.

Formulation Example 10

Present inventive composition (10) was obtained in exactly the same manner as in Formulation Example 1 except for using 11 parts of Permethrin in place of 11 parts of Pyriproxyfen.

Formulation Example 11

Present inventive composition (11) was obtained in exactly the same manner as in Formulation Example 1 except for using 11 parts of Cyphenothrin in place of 11 parts of Pyriproxyfen.

Formulation Example 12

Present inventive composition (12) was obtained in exactly the same manner as in Formulation Example 1 except for using 11 parts of Cypermethrin in place of 11 parts of Pyriproxyfen.

Formulation Example 13

Present inventive composition (13) was obtained in exactly the same manner as in Formulation Example 6 except for using 5 parts of Allethrin in place of 5 parts of Fenvalerate.

Formulation Example 14

Present inventive composition (14) was obtained in exactly the same manner as in Formulation Example 5 except for using 0.3 part of Pepol B-184 (a polyoxyethylene polyoxypropylene block polymer having a HLB of 10.1, manufactured by TOHO KAGAKU K.K) and 0.4 part of Sorpol CA-42 (a polyoxyethylene castor oil, manufactured by TOHO KAGAKU K.K) in place of 0.7 part of Soprophor 796/P.

Formulation Example 15

Present inventive composition (15) was obtained in exactly the same manner as in Formulation Example 5 except for changing the amount of Soprophor 796/P from 0.7 part to 0.5 part and using 0.6 part of Sorpol CA-42 in addition thereto.

Formulation Example 16

Present inventive composition (16) was obtained in exactly the same manner as in Formulation Example 1 except for using 11 parts of Fenitrothion in place of 11 parts of Pyriproxyfen.

Formulation Example 17

Present inventive composition (17) was obtained in exactly the same manner as in Formulation Example 1 except for using 11 parts of Cyanophos in place of 11 parts of Pyriproxyfen.

Formulation Example 18

Present inventive composition (18) was obtained in exactly the same manner as in Formulation Example 1 except for using 11 parts of Fenobucarb in place of 11 parts of Pyriproxyfen.

Formulation Example 19

Present inventive composition (19) is obtained by thoroughly mixing the following ingredients in a total amount of 100 parts: 12 parts of Pyriproxyfen, 0.7 part of Soprophor 796/P, 6 parts of Geronol FF-4-E, 33 parts of methyl oleate and the balance of Solvesso 150.

Formulation Example 20

Present inventive composition (20) is obtained by thoroughly mixing the following ingredients in a total amount of 100 parts: 11 parts of Pyriproxyfen, 0.7 part of Soprophor 796/P, 0.88 part of Soprophor CY/8 (a polyoxyethylene tristyrylphenyl ether, manufactured by Rhone Poulenc), Rhodacal 60/BE (a surfactant containing 60 wt % calcium dodecylbenzenesulfonate, manufactured by Rhone Poulenc), 33 parts of methyl oleate and the balance of Solvesso 150.

Formulation Example 21

Present inventive composition (21) is obtained by thoroughly mixing the following ingredients in a total amount of 100 parts: 11 parts of Pyriproxyfen, 1.0 part of Soprophor 796/P, 0.84 part of Soprophor CY/8, 4.67 parts of Rhodacal 60/BE, 22 parts of methyl oleate and the balance of Solvesso 150.

Next, formulations used for comparison in the test examples described hereinafter are described below as comparative formulation examples.

Comparative Formulation Example 1

Reference composition (1) was obtained by 20 thoroughly mixing the following ingredients in a total amount of 100 parts: 11 parts of Pyriproxyfen, 2.2 parts of Soprophor 796/P, 8.8 parts of Soprophor BSU (a polyoxyethylene tristyryl ether, manufactured by Rhone Poulenc), 30 parts of methyl oleate and the balance of Solvesso 150.

Comparative Formulation Example 2

Reference composition (2) was obtained in exactly the same manner as in Formulation Example 1 except for changing the amount of methyl oleate from 22 parts to 60 parts.

The stability of dilutions of the present inventive compositions with water is shown with the following test examples.

Test Example 1

In a 100-ml measuring cylinder having a stopper and filled with 500 ppm hard water was put 0.1 ml of each of the present inventive compositions (1) to (6) and reference compositions (1) and (2) obtained above. Then, each measuring cylinder was turned upside down at a rate of 30 times per minute to mix the content uniformly, after which it was allowed to stand. One hour after the start of the standing, whether the mixture had been phase-separated or not was observed. The results obtained are shown in Table 1.

In Table 1, the symbols A, B, C and D used as indications of emulsion stability have the following meanings:

A: no phase-separation of the mixture,

B: very slight phase-separation of the mixture,

C: apparent phase-separation of the mixture,

D: marked phase-separation of the mixture.

Test Example 2

In a glass bottle was put 30 ml of each of the present inventive compositions (1) to (6) and reference compositions (1) and (2) obtained above, and stored at −5° C. for 2 weeks, after which the existence of a precipitate was investigated. The results obtained are shown in Table 1 together with the results of Test Example 1.

In Table 1, the symbols −, +, ++, +++ and ++++ used as indications of low-temperature stability have the following meanings:

−: no precipitate,

+: a very small amount of a precipitate,

++: a precipitate in an intermediate amount between + and +++,

+++: a precipitate in an intermediate amount between ++ and ++++,

++++: a large amount of a precipitate.

TABLE 1

| Test composition | Emulsion stability | Low-temperature stability |
|---|---|---|
| Present inventive composition (1) | A | − |
| Present inventive composition (2) | A | −~+ |
| Present inventive composition (3) | A | − |
| Present inventive composition (4) | A | − |
| Present inventive composition (5) | A | − |
| Present inventive composition (6) | A | −~+ |
| Reference composition (1) | D | ++ |
| Reference composition (2) | D | ++++ |

Test Example 3

A test for eye-irritating properties of the present inventive compositions (1) and (2) obtained above was carried out as follows.

The eyes of a rabbit were treated with 0.1 ml of each test composition and lightly shut for 1 second. After about 30 seconds, the eyes were washed by spraying 300 ml of tepid water for 1 minute. After 1 week, the degree and area of corneal opacity were investigated to find that neither of present inventive compositions (1) and (2) had caused corneal opacity.

Effect of the Invention

The composition of the present invention is a pesticidal composition which shows a good emulsion stability when diluted with water, has a good low-temperature storage stability, and is only slightly irritant.

What is claimed is:

1. A pesticidal composition comprising
   (a) 1 to 50% by weight of a lipophilic compound as a pesticidally active ingredient,
   (b) 0.1 to 10% by weight of at least one nonionic surfactant,
   (c) 0.3 to 4% by weight of at least one anionic surfactant selected from the group consisting of alkylarylsulfonic acid salts and alkylbiphenylsulfonic acid salts, (d) 15 to 40% by weight of a fatty acid ester represented by the formula:

RCOOR'  [1]

wherein R is an alkyl group having 2 to 21 carbon atoms or an alkenyl group having 2 to 21 carbon atoms, and R' is an alkyl group having 1 to 6 carbon atoms, and (e) 20 to 80% by weight of an aromatic hydrocarbon solvent, wherein the weight percentages are based on the total weight of the pesticidal composition.

2. A pesticidal composition according to claim 1, wherein the nonionic surfactant (b) is selected from the group consisting of polyoxyethylene polyoxypropylene block polymers, polyoxyethylene polyoxypropylene alkyl aryl ethers, polyoxyethylene polyoxypropylene alkyl ethers, polyoxyethylene polyoxypropylene polyaryl ethers, and fatty acid esters of polyoxyethylene polyoxypropylene block polymers.

3. A pesticidal composition according to claim 2, wherein the nonionic surfactant (b) is selected from the group consisting of polyoxyethylene polyoxypropylene block polymers having a hydrophilic-lipophilic balance of 10 to 14, polyoxyethylene polyoxypropylene alkyl aryl ethers having a hydrophilic-lipophilic balance of 9 to 14, polyoxyethylene polyoxypropylene ethers having a hydrophilic-lipophilic balance of 9 to 12, polyoxyethylene polyoxypropylene polyaryl ethers having a hydrophilic-lipophilic balance of 9 to 14, and fatty acid esters of polyoxyethylene polyoxypropylene block polymers having a hydrophilic-lipophilic balance of 9 to 13.

4. A pesticidal composition according to claim 1, 2 or 3, wherein the lipophilic compound as a pesticidally active ingredient (a) is Pyriproxyfen.

5. A pesticidal composition according to claim 1, 2 or 3, wherein the lipophilic compound as a pesticidally active ingredient (a) is a pyrethroid compound.

6. A pesticidal composition according to claim 1, 2 or 3, wherein the lipophilic compound as a pesticidally active ingredient (a) is a compound represented by the formula:

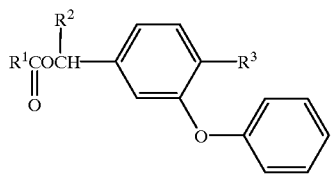
[2]

wherein $R^1$ is a group represented by the formula:

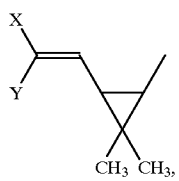
[3]

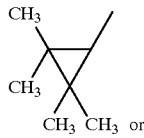
[4]

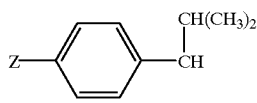
[5]

(wherein X and Y, which may be the same or different, are methyl groups, trifluoromethyl groups, halogen atoms or alkoxycarbonyl groups whose alkoxy group has 1 to 4 carbon atoms, and Z is a halogen atom or a difluoromethoxy group), $R^2$ is a hydrogen atom or a cyano group, and $R^3$ is a hydrogen atom or a fluorine atom.

7. A pesticidal composition according to claim 1, 2 or 3, wherein the lipophilic compound as a pesticidally active ingredient (a) is an organophosphorus compound.

8. A pesticidal composition according to claim 1, 2 or 3, wherein the lipophilic compound as a pesticidally active ingredient (a) is a carbamate compound.

9. A pesticidal composition according to claim 1, 2 or 3, wherein the lipophilic compound as a pesticidally active ingredient (a) is selected from the group consisting of Pyriproxyfen, Fenpropathrine, Fenvalerate, Permethrin, Cyphenothrin, Cypermethrin, Allethrin, Fenitrothion, Cyanophos and Fenobucarb.

10. A pesticidal composition according to any one of claims 1 to 3, wherein the anionic surfactant (c) is an alkylbenzenesulfonic acid.

11. A pesticidal composition according to any one of claims 1 to 3, wherein the fatty acid ester (d) is oleic acid ester or lauric acid ester.

12. A pesticidal composition according to any one of claims 1 to 3, wherein the weight ratio of the fatty acid ester (d) to the aromatic hydrocarbon solvent (e) ranges from 1:5 to 1:1.

13. A pesticidal composition according to claim 4, wherein the anionic surfactant (c) is an alkylbenzenesulfonic acid.

14. A pesticidal composition according to claim 5, wherein the anionic surfactant (c) is an alkylbenzenesulfonic acid.

15. A pesticidal composition according to claim 6, wherein the anionic surfactant (c) is an alkylbenzenesulfonic acid.

16. A pesticidal composition according to claim 7, wherein the anionic surfactant (c) is an alkylbenzenesulfonic acid.

17. A pesticidal composition according to claim 8, wherein the anionic surfactant (c) is an alkylbenzenesulfonic acid.

18. A pesticidal composition according to claim 9, wherein the anionic surfactant (c) is an alkylbenzenesulfonic acid.

19. A pesticidal composition according to claim 4, wherein the fatty acid ester (d) is oleic acid ester or lauric acid ester.

20. A pesticidal composition according to claim 5, wherein the fatty acid ester (d) is oleic acid ester or lauric acid ester.

21. A pesticidal composition according to claim 6, wherein the fatty acid ester (d) is oleic acid ester or lauric acid ester.

22. A pesticidal composition according to claim 7, wherein the fatty acid ester (d) is oleic acid ester or lauric acid ester.

23. A pesticidal composition according to claim 8, wherein the fatty acid ester (d) is oleic acid ester or lauric acid ester.

24. A pesticidal composition according to claim 9, wherein the fatty acid ester (d) is oleic acid ester or lauric acid ester.

25. A pesticidal composition according to claim 4, wherein the weight ratio of the fatty acid ester (d) to the aromatic hydrocarbon solvent (e) ranges from 1:5 to 1:1.

26. A pesticidal composition according to claim 5, wherein the weight ratio of the fatty acid ester (d) to the aromatic hydrocarbon solvent (e) ranges from 1:5 to 1:1.

27. A pesticidal composition according to claim 6, wherein the weight ratio of the fatty acid ester (d) to the aromatic hydrocarbon solvent (e) ranges from 1:5 to 1:1.

28. A pesticidal composition according to claim 7, wherein the weight ratio of the fatty acid ester (d) to the aromatic hydrocarbon solvent (e) ranges from 1:5 to 1:1.

29. A pesticidal composition according to claim 8, wherein the weight ratio of the fatty acid ester (d) to the aromatic hydrocarbon solvent (e) ranges from 1:5 to 1:1.

30. A pesticidal composition according to claim 9, wherein the weight ratio of the fatty acid ester (d) to the aromatic hydrocarbon solvent (e) ranges from 1:5 to 1:1.

31. The pesticidal composition according to claim 1, wherein the anionic surfactant (c) is an alkylbiphenyl sulfonic acid salt.

32. The pesticidal composition according to one of claim 1 or 3, wherein the pesticidally active ingredient is an insecticide or an insect growth regulator.

* * * * *